(12) United States Patent
Lu et al.

US009322807B2

(10) Patent No.: US 9,322,807 B2
(45) Date of Patent: Apr. 26, 2016

(54) ULTRASONIC SIGNAL TIME-FREQUENCY DECOMPOSITION FOR BOREHOLE EVALUATION OR PIPELINE INSPECTION

(71) Applicant: Halliburton Energy Services, Inc., Houston, TX (US)

(72) Inventors: Yinghui Lu, The Woodlands, TX (US); Arthur Cheng, Houston, TX (US); Zhijuan Zhang, Houston, TX (US); Tatiana Gilstrap, The Woodlands, TX (US); Rob Epstein, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/427,773

(22) PCT Filed: Apr. 16, 2014

(86) PCT No.: PCT/US2014/034314
§ 371 (c)(1),
(2) Date: Mar. 12, 2015

(87) PCT Pub. No.: WO2015/160340
PCT Pub. Date: Oct. 22, 2015

(65) Prior Publication Data
US 2015/0338378 A1 Nov. 26, 2015

(51) Int. Cl.
*G01N 29/04* (2006.01)
*E21B 47/12* (2012.01)
(Continued)

(52) U.S. Cl.
CPC ............... *G01N 29/04* (2013.01); *E21B 47/12* (2013.01); *E21B 47/14* (2013.01); *G01V 1/40* (2013.01); *G01N 2291/269* (2013.01)

(58) Field of Classification Search
CPC ....... G01N 29/50; G01N 29/04; G01N 29/46; G01N 29/4409; G01N 29/38; G01N 29/36; G01N 29/42; G01N 29/44; G01V 1/40; G01V 1/44; G01V 1/48; G01V 1/50
USPC ................................. 73/632, 152.16, 10, 612
See application file for complete search history.

(56) References Cited

U.S. PATENT DOCUMENTS 4,709,357 A * 11/1987 Maki, Jr. ................. G01V 1/48
181/105
5,216,638 A * 6/1993 Wright ................ E21B 47/0005
367/30

(Continued)

FOREIGN PATENT DOCUMENTS

EP 1040251 B1 1/2012
NO WO-01/69286 A2 9/2001
(Continued)

OTHER PUBLICATIONS

Lu, Yinghui, et al., "Numerical Implementation of Matching Pursuit for the Analysis of Complex Ultrasonic Signals", *IEEE Transactions on Ultrasonics, Ferroelectrics, and Frequency Control*, 55(1), (2008), 173-182.
Lu, Yinghui, et al., "Ultrasonic Signal Decompensation Via Matching Pursuit With an Adaptive and Interpolated Dictionary", *Review of Progress in Quantitative Nondestructive Evaluation*vol. 26A, Thompson, D.O., et al., Editors, (2007), 579-586.
"International Application Serial No. PCT/US2014/034314, International Search Report mailed Jan. 14, 2015", 3 pgs.
"International Application Serial No. PCT/US2014/034314, Written Opinion mailed Jan. 14, 2015", 6 pgs.

*Primary Examiner* — Lisa Caputo
*Assistant Examiner* — Philip Cotey
(74) *Attorney, Agent, or Firm* — Schwegman, Lundberg & Woessner, P.A.; Benjamin Fite (57) ABSTRACT

In some embodiments, methods, apparatus, and systems may operate to launch acoustic waves along a first acoustic path length from an acoustic transducer. The apparatus receives a reflected signal in response to each acoustic wave, each reflected signal including at least one echo. The reflected signal is decomposed, using a time-frequency decomposition method with basis functions, into a wavelet associated with each echo. Parameters describing each associated wavelet are determined and a borehole evaluation or pipeline inspection is performed based on the parameters.

20 Claims, 7 Drawing Sheets

(51) Int. Cl.
 *E21B 47/14* (2006.01)
 *G01V 1/40* (2006.01)

(56) References Cited

U.S. PATENT DOCUMENTS

| | | | | |
|---|---|---|---|---|
| 5,970,798 | A | * | 10/1999 | Gleman ................. G01L 5/246 73/761 |
| 5,995,447 | A | * | 11/1999 | Mandal .................... G01V 1/44 181/106 |
| 6,470,749 | B1 | * | 10/2002 | Han ....................... G01B 17/02 73/609 |
| 6,745,129 | B1 | | 6/2004 | Li et al. |
| 6,856,936 | B1 | | 2/2005 | Chen et al. |
| 7,603,238 | B2 | | 10/2009 | Valero et al. |
| 2003/0114989 | A1 | | 6/2003 | Blanch et al. |
| 2004/0100282 | A1 | * | 5/2004 | Christensen ......... G01B 17/025 324/644 |
| 2008/0210010 | A1 | * | 9/2008 | Orth ..................... G01N 29/041 73/592 |
| 2013/0247673 | A1 | * | 9/2013 | Davis .................... G01B 17/02 73/632 |
| 2014/0107954 | A1 | * | 4/2014 | Lih .................... G01N 29/4472 702/54 |

FOREIGN PATENT DOCUMENTS

| | | |
|---|---|---|
| WO | WO-2007/050680 A2 | 5/2007 |
| WO | WO-2013081608 A1 | 6/2013 |
| WO | WO-2014011180 A1 | 1/2014 |
| WO | WO-2015160340 A1 | 10/2015 |

\* cited by examiner

Fig. 7

ULTRASONIC SIGNAL TIME-FREQUENCY DECOMPOSITION FOR BOREHOLE EVALUATION OR PIPELINE INSPECTION

PRIORITY APPLICATIONS

This application is a U.S. National Stage Filing under 35 U.S.C. 371 from International Application No. PCT/US2014/034314, filed on 16 Apr. 2014; which application is incorporated herein by reference in its entirety.

BACKGROUND

After drilling operations, borehole casings can be used to help stabilize the well. The casing is cemented to assure zonal isolation and sustain its stability. Over time deterioration and/or imperfections in the casing and/or cement can cause the borehole to collapse and/or fluids to migrate therefore compromising the zonal isolation.

Fluid (e.g., oil, gas) pipelines can be used to transport the fluids for long distances from one location to another. Environmental factors and fluid chemicals can result in corrosion of the pipeline inside and outside, thus weakening the pipeline walls. Improper welding of the pipeline sections can also result in leaking of the fluid into the surrounding environment. It can thus be desirable to be able to determine the integrity of a borehole casing or a fluid pipeline.

DETAILED DESCRIPTION

Ultrasound wave propagation can be used as part of an interrogation method for borehole evaluation or fluid pipeline inspection. The interrogation method can be used in either a pulse-echo configuration or a pitch-catch configuration.

In order to obtain borehole information from measured ultrasonic signals, such as casing inside diameter (ID), casing thickness, cement bonding impedance, and a borehole image, the identity or estimate of discrete reflected/reverberation echoes from the measured ultrasonic signals can be determined. Inspection of pipeline integrity, including pipeline ID, pipeline thickness, corrosion, and weld condition, can be accomplished by separating ultrasonic echoes and/or wave packages from the measured signals. Embodiments disclosed herein use ultrasonic signal time-frequency decomposition (e.g., a matching pursuit signal decomposition, wavelet transform method), in order to decompose a measured ultrasonic signal into discrete wavelets. Each discrete wavelet can represent values of arrival time, frequency, and amplitude for received physical echoes (e.g., wave packages). The arrival time and/or frequency and/or amplitude represented by the wavelets can then be used to calculate information regarding the physical condition of the casing or pipeline and the cement casing bonding impedance. The decomposed wavelets can also be used to compress the measured waveforms for the purposes of data storage and telemetry. The compressed waveforms can then be stored.

Figure 1:
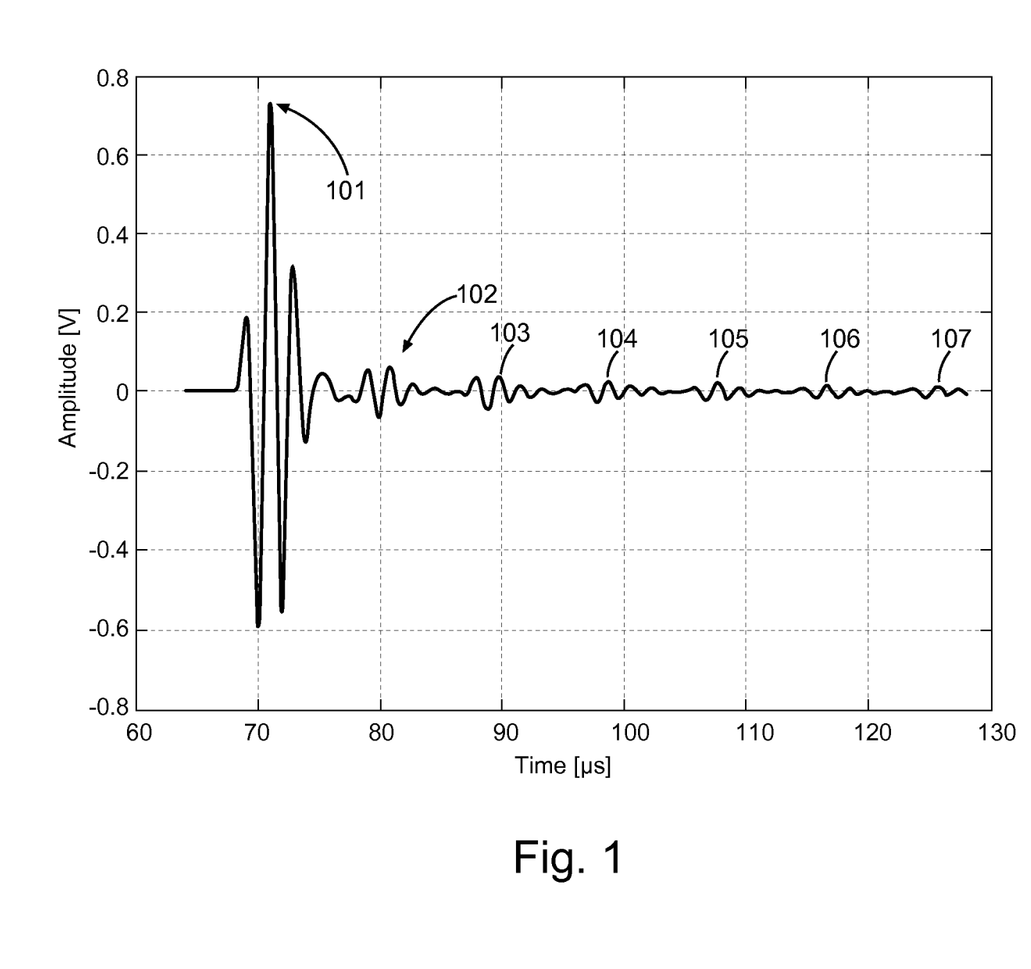
FIG. 1 is a plot illustrating amplitude versus time of a series of wavelets in accordance with aspects of the present disclosure.

As used herein, a wavelet can be defined as a received echo signal that results from a transmitted ultrasonic signal. The echo signal (e.g., wavelet) may have bounced back from the inside wall of a casing or pipeline, the outside wall of the casing or pipeline, and/or imperfections in the casing or pipeline. For example, FIG. 1 illustrates a plot of amplitude (volts) versus time (microseconds) of a series of wavelets 101-107 that have resulted from transmission of an ultrasonic signal.

Figure 2:
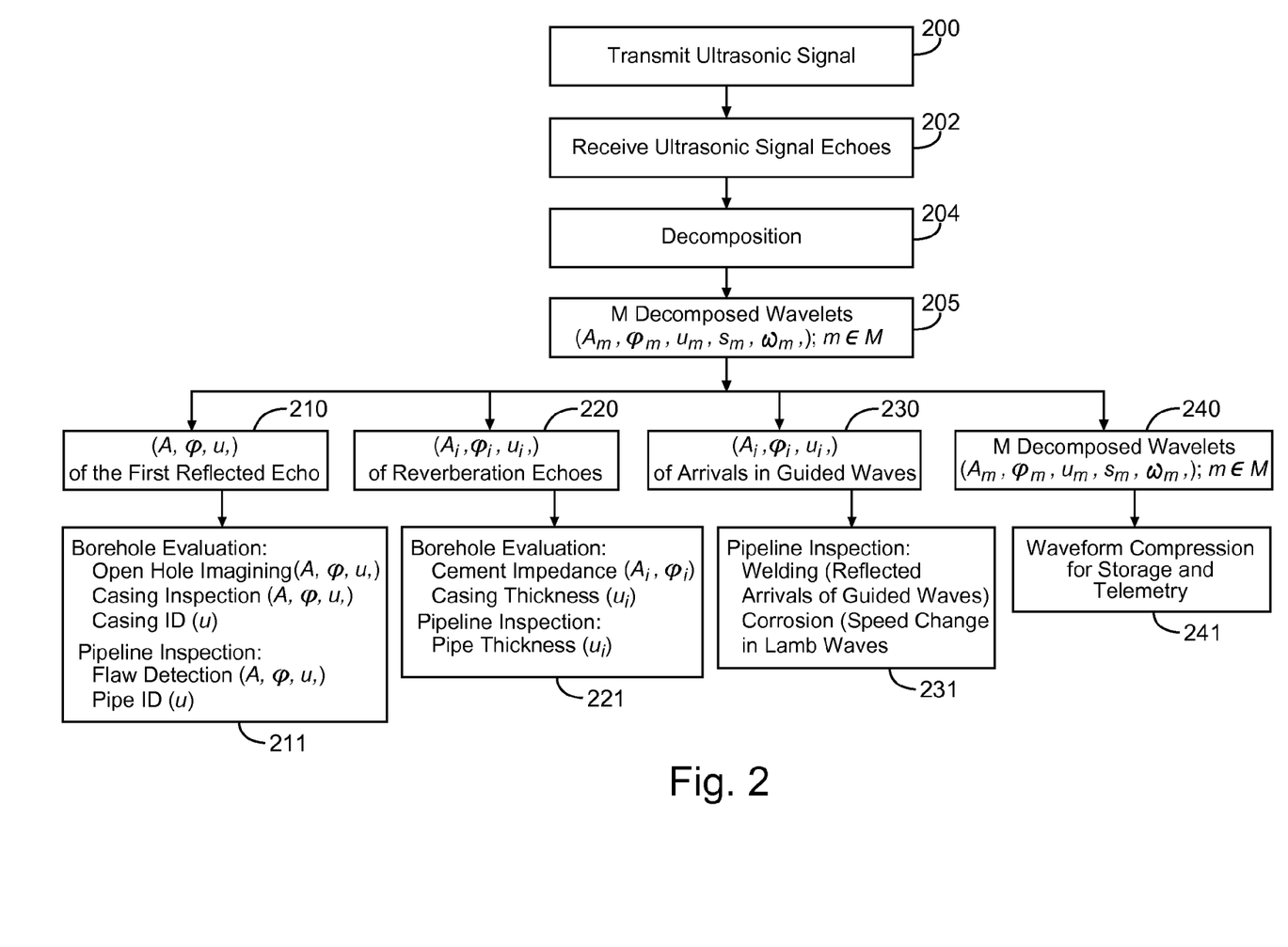
FIG. 2 is a flowchart illustrating an embodiment of a method for ultrasonic signal decomposition for borehole evaluation or pipeline inspection in accordance with aspects of the present disclosure.

FIG. 2 illustrates a flowchart of an embodiment of a method for borehole evaluation and pipeline inspection using ultrasonic signals. An ultrasonic signal (e.g., frequency >20 kHz) is transmitted 200 in some manner (e.g., using pitch-catch, or pulse echo techniques). The reflected ultrasonic signal echo is then received 202. See FIG. 4 for an example of an apparatus capable of performing transmission and reception of an ultrasonic signal according to the methods described herein.

The received ultrasonic signal can then be decomposed 204. The decomposition can be a time-frequency decomposition, such as matching pursuit or traditional wavelet decomposition. The decomposition can have a set of basis functions that are substantially similar to the physical echoes (e.g., wavelets) in waveform shape.

Matching pursuit is a signal decomposition method whereby a signal is decomposed into a linear combination of basis functions that are selected from a redundant dictionary. The purpose of using redundant basis functions is to maximize the waveform matching between the basis functions and the signal, which may not be achieved if the basis functions are restricted by orthogonality, as occurs with discrete wavelet decomposition.

The following description of the decomposition of the received signal into wavelets uses Gabor functions for purposes of illustration only. The present embodiments are not limited to any one basis function type for decomposing the received signal. Other embodiments can use more than one basis function type.

A family of basis functions (e.g., Gabor functions) are shown subsequently, and each received signal can be matched with the best function from the family of functions. The family of modified Gabor functions can be used as the basis functions for methods described herein since Gabor functions can be qualitatively and quantitatively very similar to ultrasonic echoes and wave packages. Modified Gabor functions retain the waveform shape of their respective Gabor functions, but render the proposed decomposition translation invariant (i.e., a shift of the original signal in time does not change the decomposed wavelets except for the same amount of shift in time in each decomposed wavelet). This is a desirable property for stable decomposition of a measured signal in the presence of measurement errors and noise.

Each modified Gabor function is a product of a Gaussian function with an in-phase, complex sinusoid and is specified by arrival time, scaling factor, and frequency, denoted by u, s, and $\omega$, respectively. For example, one such Gabor function can be represented by:

$$g(t) = \frac{1}{\sqrt{2\pi} * s} e^{\frac{(t-u)^2}{2s^2}} e^{i\omega(t-u)}$$

The M decomposed wavelets can be denoted by $(A_m, \phi_m, u_m, s_m, \omega_m)$ where m∈M 205 if the measured signal is decomposed into M wavelets where $(A_m, \phi_m)$ are the weights (amplitude and phase) for each decomposed wavelet.

By performing a cross-correlation between each wavelet and the Gabor basis function, the arrival time (u) of the wavelet at the receiver, the phase (ϕ) of the wavelet, and the amplitude (A) of the wavelet can be determined. These parameters (A, ϕ, u) can be used for borehole evaluation and pipeline inspection.

Referring again to FIG. 2, the (A, ϕ, u) parameters of the first wavelet (e.g., see reflected echo 101 of FIG. 1) have been determined 210 as discussed previously. The (A, ϕ, u) parameters of the first wavelet 101 can be used for borehole evaluation 211 such as open hole imaging, casing inspection, and casing ID. The (A, ϕ, u) parameters of the first wavelet can also be used for pipeline inspection 211 such as flaw detection and pipeline ID determination. The casing and pipeline ID determinations may use only the arrival time (u) of the first wavelet in some embodiments.

The $(A_i, \phi_i, u_i)$ parameters of reverberation wavelets (e.g., see reflected echoes 102-107 of FIG. 1) have been determined 220 as discussed previously. These wavelets 102-107 are typically the echoes resulting from within the casing and pipeline walls. Thus, the $(A_i, \phi_i, u_i)$ parameters can be used to determine cement impedance and casing thickness during a borehole evaluation and pipeline thickness during a pipeline inspection 221. The casing and pipeline thickness evaluations may only use the arrival time $(u_i)$ parameter while the cement impedance may only use the amplitude and phase parameters $(A_i, \phi_i)$. The amplitudes of the sequence of reverberations are determined by the impedance of the cement-casing bonding. This relationship is defined by the reflectivity series:

$$R = R_{12} + T_{12} R_{23} T_{21} e^{-i2k_c d} (1 + R_{21} R_{23} e^{-i2k_c d} + R_{21}^2 R_{23}^2 e^{-i4k_c d} + \dots)$$

where $R_{ij}$ and $T_{ij}$ are the reflection and transmission coefficients, respectively; d refers to the casing thickness and $k_c$ is the wavenumber. The i and j indices (i.e. 1, 2 and 3) refer to the layers of fluid, steel and cement respectively. Each R and T is defined by the impedance contrast between the layers. As the impedance contrast between cement and steel changes, the rate of decay of the reverberations amplitudes and energy change. Thus, to determine the impedance, the wavelet is constrained and the energy and estimate of the energy decay is determined.

The $(A_i, \phi_i, u_i)$ parameters of guided wave arrivals have been determined 230 as discussed previously. The guided wave arrivals can result from transmission of the ultrasonic signal within the wall of a pipeline. Because the pipe wall is a wave guide, the waves propagating within the pipeline wall can be referred to as guided waves and the properties of the guided waves can be affected by the wave guide (i.e., the pipe wall). This is the principle that can be used for pipeline inspection 231. The matching pursuit method above can be used to extract useful information (e.g., $A_i, \phi_i, u_i$) from the received guided waves to infer the integrity of the pipe. For example, the pipeline inspection can include pipeline welding integrity (i.e., determined according to reflected arrivals of guided wavelets) and pipeline corrosion (i.e., determined according to speed change in the guided wavelets).

The M decomposed wavelet parameters $(A_m, \phi_m, u_m, s_m, \omega_m)$, where m∈M, have been determined 240 as discussed previously. The wavelet parameters can be stored and/or propagated via telemetry 241 to be used in analyzing the wavelets by one or more processors located in a wireline tool or on the surface. As discussed previously, u is the arrival time of a wavelet at the receiver, ϕ is the phase of the wavelet at the receiver, A is the amplitude of the wavelet at the receiver, ω is the frequency of the wavelet, and s is a scaling factor.

Figure 3:
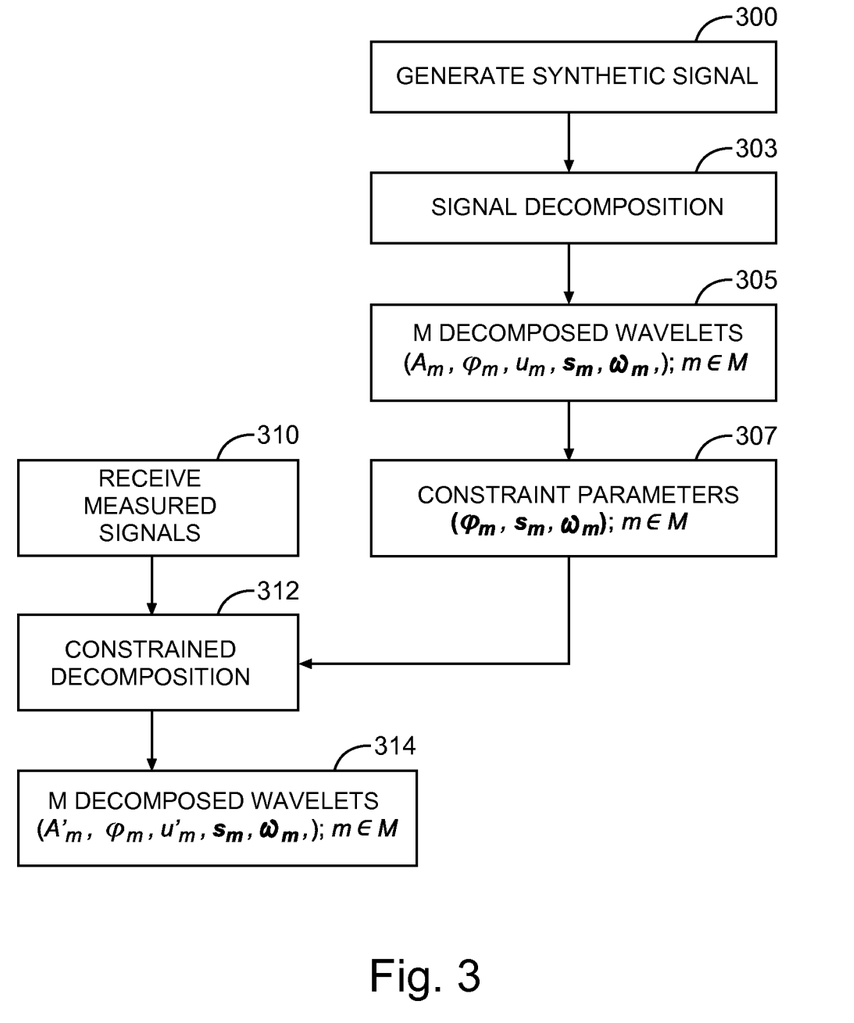
FIG. 3 is a flowchart illustrating another embodiment of the method for ultrasonic signal decomposition for borehole evaluation or pipeline inspection in accordance with aspects of the present disclosure.

FIG. 3 illustrates a flowchart of another embodiment of the method for borehole evaluation or pipeline inspection using ultrasonic signals. This embodiment incorporates information from a theoretical model into the decomposition of the received signal (e.g., matching pursuit method). For example, synthetic waveforms can be incorporated into the decomposition of a measured signal (e.g., received signal) to find the amplitude (A) and arrival time (u) of reverberation echoes (e.g., wavelets) more robustly in the presence of measurement outliers.

The method calculates a synthetic reverberation signal 300 using a theoretical model based on certain prior information. For example, the prior information can include a physical model of the pipeline, including a layer of fluid in the pipe followed by a layer of steel followed by a layer of fluid outside the pipe. Each layer can be characterized by specific acoustic properties including speed and impedance. The physical model may also incorporate a specific radiation pattern of the transducer and curvature of the pipe. The synthetic signal can then be decomposed into M wavelets 303. In an embodiment, the decomposition can be performed using matching pursuit decomposition as previously described. The resulting M decomposed wavelet parameters include $(A_m, \phi_m, u_m, s_m, \omega_m)$, where m∈M 305. The parameters $(\phi_m, s_m, \omega_m)$, where m∈M, of the decomposed wavelets, define their respective waveform shapes and $(A_m, u_m)$, where m∈M, define the magnitudes and arrival times.

The phase, scaling factor, and frequency $(\phi_m, s_m, \omega_m)$, where m∈M, from the synthetic signal are determined to be constraint parameters 307. When a measured signal is received 310, the constraint parameters can be used during the decomposition of the measured signal 312 so that the shapes of the basis function are kept the same for the decomposition of the measured signal. Such constraints can be indicated as: $(\phi'_m = \phi_m, s'_m = s_m, \omega'_m = \omega_m)$, where m∈M. With these constraints, the decomposition leads to a set of decomposed wavelets 314 that can be quantified by $(A'_m, \phi_m, u'_m, s_m, \phi_m)$, where m∈M, where only the amplitude $(A'_m)$ and arrival time $(u'_m)$ are fitted from the measured signal.

In another embodiment, an additional constraint, $|u'_m - u_m| = \delta_m$, can be placed on the time shift $u'_m$ of each modified Gabor function. The value of $\delta_m$ is set to prevent a matching Gabor function from jumping to another portion of the measure signal, so that its value stays in the vicinity of values produced by the original Gabor function. The determined values may then be used for pipeline and borehole inspection.

Figure 4:
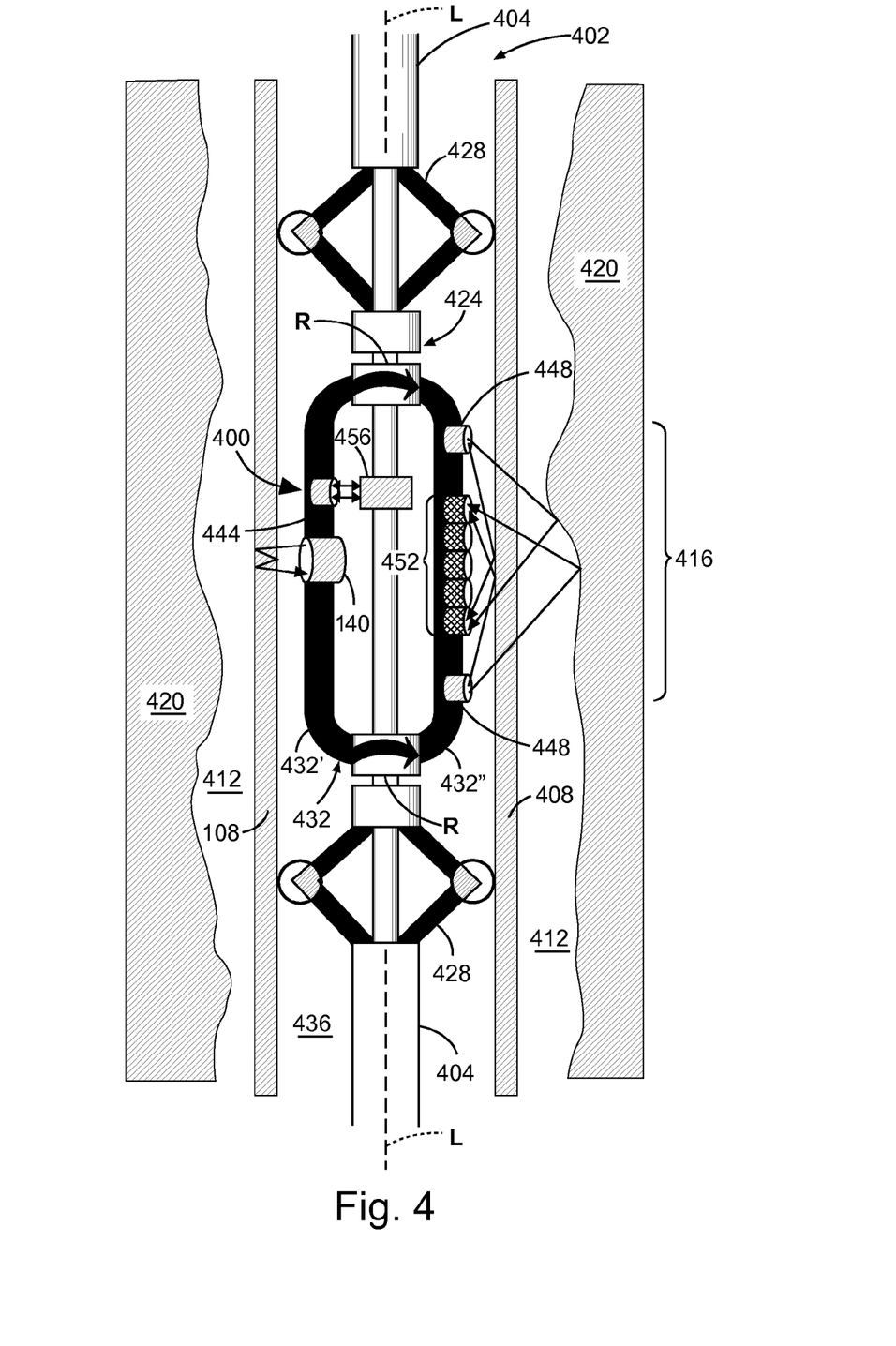
FIG. 4 is a diagram illustrating an apparatus and inspection tool according to various embodiments.

FIG. 4 is a side view of an apparatus 400 and inspection tool 402 according to various embodiments. While the subsequent discussion of the inspection tool 402 focuses on borehole evaluation, other embodiments can use a substantially similar tool to perform pipeline inspections.

The inspection tool 402 may comprise an ultrasonic tool with a housing 404 coupled to a rotatable mount 424 for borehole evaluation (e.g., casing 408 and cement 412 condition) or pipeline inspection. The rotatable mount 424 is attached in turn to a pulse-echo device 440 (e.g., a pulse-echo circumferential acoustic scanning tool (CAST) transducer), and a pitch-catch array 416 that, for purposes of illustration, includes two transmitters 448 and five receivers 452. Other embodiments may use either the pulse-echo device 400 or the pitch-catch device 416.

The rotatable mount 424 is also attached to the apparatus 400, which comprises another pulse-echo device 444 (e.g., a second pulse-echo transducer) for velocity measurement in a fluid 436 (e.g., mud), and a dual-faced target 456 that provides at least two different propagation distances through the fluid 436, which can be averaged to provide a better measurement of the fluid velocity.

The pitch-catch array 416 and the pulse-echo device 440 can receive reflected signals (e.g., measured signals) resulting from transmitted ultrasonic signals. The measured signal can be decomposed by the above-described method in order to perform the borehole evaluation or pipeline inspection.

The array 416 can include transmitters 448 and receivers 452 that extend along the length of the axis of rotation L, which is substantially aligned with the longitudinal axis of the housing 404. The rotatable mount 424 (e.g., an in-line rotatable head) is shown with in-line centralizers 428, which allows the rotatable mount 424 to be located at any point in a logging tool string. One or more inline centralizers 428 may be disposed between the housing 404 and the rotatable mount 424. The rotatable mount 424 can comprise a framework 432 having two or more arms (two arms are shown—a first arm 432' and a second arm 432") approximately horizontally opposed across the longitudinal axis of the housing 404. The pulse-echo devices 440, 444 may be attached to the first arm 432', and the array 416 may be attached to the second arm 432".

The weight of the individual arms 432', 432" may be adjusted to balance the weight of various components (e.g., transducers, such as the array 416) attached to the arms 432', 432", to impart rotational stability to the rotatable mount 424. The arms 432', 432" may be provided with a fluid dynamic profile design to reduce drag in the borehole fluid 436 while rotating. The framework 432 may permit radial expansion and contraction, to operate more easily in different sizes of the borehole.

By using the array 416, cement evaluation with imaging behind the casing 408 may be accomplished more easily. Both pitch-catch (e.g., in the array 416) and pulse-echo devices 440 (e.g., a pulse-echo transducer) can be used to assess the integrity of the cement 412 behind the casing 408. For example, the pulse-echo device 440 can be used to estimate the thickness of the casing 408, the borehole shape, and the impedance of the cement 412 behind the casing 408 (from the normal incidence of the ultrasonic wave). The pitch-catch array 416 can be used to help identify reflectors behind the casing 408 as part of imaging behind the casing 408, including reflectors that are not normal to the incidence wave provided by the pulse-echo device 440.

Array focusing may be used to further enhance the received reflected signals. In some embodiments, the transmitters 448 operate with a center frequency of about 50 kHz to about 150 kHz, or a broad band (impulse or chirp) pulse from about 50 kHz to about 200 kHz. The response of the receivers 452 may be selected to peak over a wider range, of about 20 kHz to about 250 kHz.

While a rotatable mount 424 is shown, the pitch-catch concept can also be applied to a non-rotating segmented transducer array assembly to image behind casing. In this case, a non-rotating array of receivers 452 with five azimuthal segments can map the interface between the cement 412 and the formation 420, although perhaps with less resolution than the rotatable mount 424 provides.

Additional transducers, including an array, may be mounted to the same framework 432 as the rotating pulse-echo device 444 that is used to determine the fluid velocity. Thus, the housing 404 may be attached to an array 416 of pitch-catch transducers mounted to a second arm 432" of a framework 432 forming a part of the rotatable mount 424, the pitch-catch transducers facing away from the axis of rotation L.

The array 416 may include multiple transmitters and receivers, wherein the receivers are shared by the transmitters. As shown in FIG. 4, the array 416 comprises two transmitters 448 and five receivers 452. Other combinations of transmitters and receivers are possible.

The pulse-echo device 444 and the array 416 may be mounted on opposite sides of the framework. Thus, the housing 404 may be fashioned so that the pulse-echo device 444 (e.g., an acoustic transducer) is mounted to a first arm 432' of the framework 432, the first arm 432' substantially opposing the second arm 432" with respect to the axis of rotation L.

Yet another device 440, perhaps operating in pulse-echo mode, may be mounted to the rotating framework 432, facing away from the axis of rotation L. Thus, the tool 402 may comprise a pulse-echo device 440 (e.g., an acoustic transducer) mounted to the first arm 432' of the framework 432, the pulse-echo device 440 facing away from the axis of rotation L. The pulse-echo device 440 may comprise a wide band transmitter so that a single transducer can be applied for a wide range of casing sizes. Further embodiments may be realized.

Figure 5:
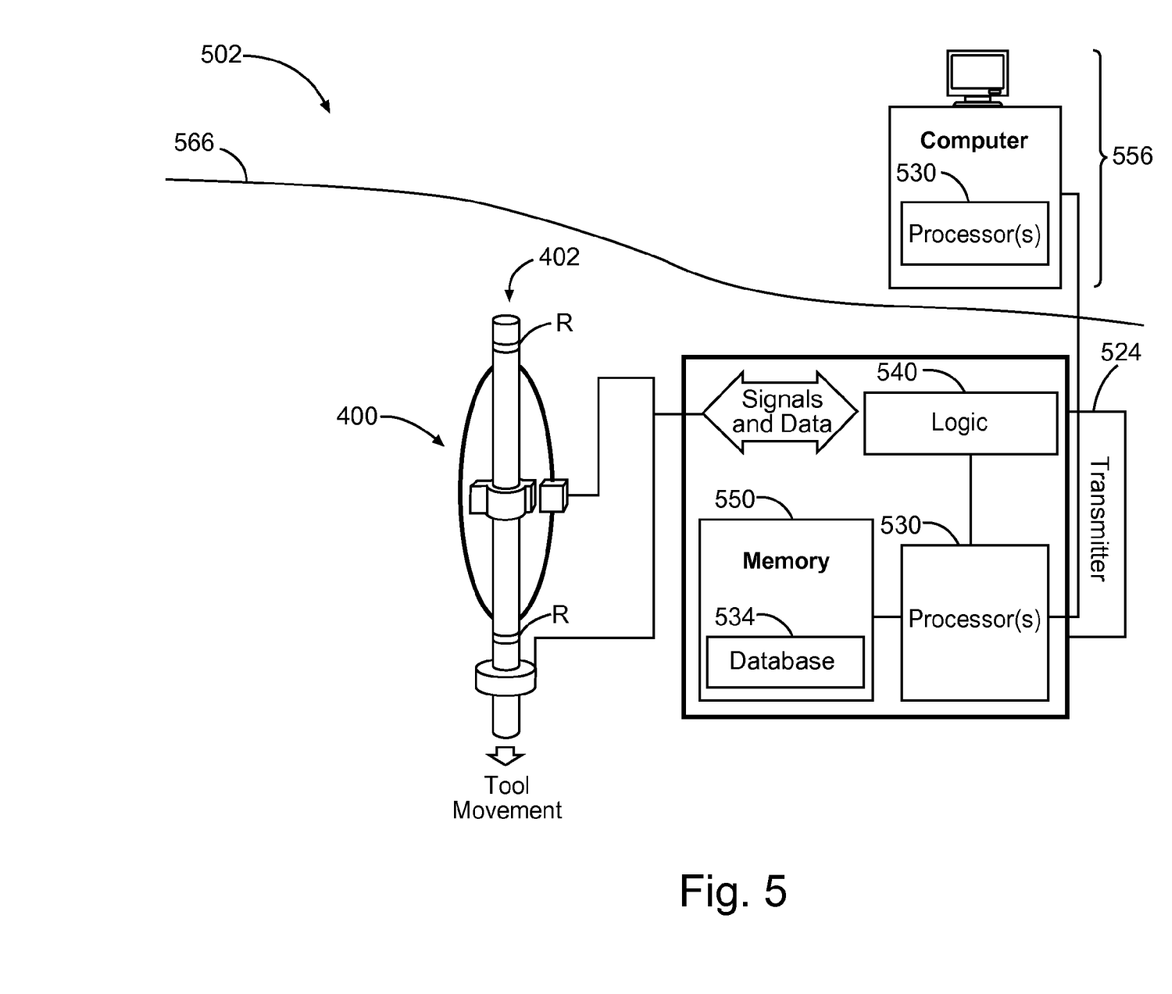
FIG. 5 is a block diagram illustrating an embodiment of a system for borehole evaluation or pipeline inspection in accordance with aspects of the present disclosure.

FIG. 5 is a block diagram of an apparatus 400 and system 502 according to various embodiments. Such a system 502 can be used for either borehole evaluation or pipeline inspection. In some embodiments, the system 502 comprises an inspection tool 402, as shown in FIG. 4, attached to one or more apparatus 400. The system 502 may further comprise one or more processors 530, located inside and/or outside the inspection tool 402, such as a wireline tool. The processor(s) 530 may be configured to perform the ultrasonic signal decomposition method for borehole evaluation and pipeline inspection. The processor(s) 530 can include microcontrollers or other controller circuits. The processor(s) 530 that can be included in a tool.

Other components of the system 502 may include memory 550 and data acquisition logic 540. The memory 550 is communicatively coupled to the processor(s) 530. The processor(s) 530, memory 550, and logic 540 may form part of a data acquisition system, where a database 534 is used to store waveform telemetry that results from the above-described method for ultrasonic signal decomposition for borehole evaluation or pipeline inspection.

The processor(s) 530 can execute instructions stored in the memory to receive a reflected signal from an acoustic receiver, decompose the reflected signal into at least one wavelet using the time-frequency decomposition and set of basis functions as described previously, determine parameters associated with each wavelet, and perform the borehole evaluation or pipeline inspection based on the parameters. The decomposition can be performed at a surface processor once data from the tool is received.

A data transmitter 524 may be used to transmit acquired data values and/or processing results to the surface 566. Thus, the system 502 may comprise a data transmitter 524 (e.g., a telemetry transmitter) to transmit acquired echo data to a surface workstation 556. The data transmitter 524 can be either wireless or wireline (e.g., wire, fiber optics). Additional embodiments may be realized.

Figure 6:
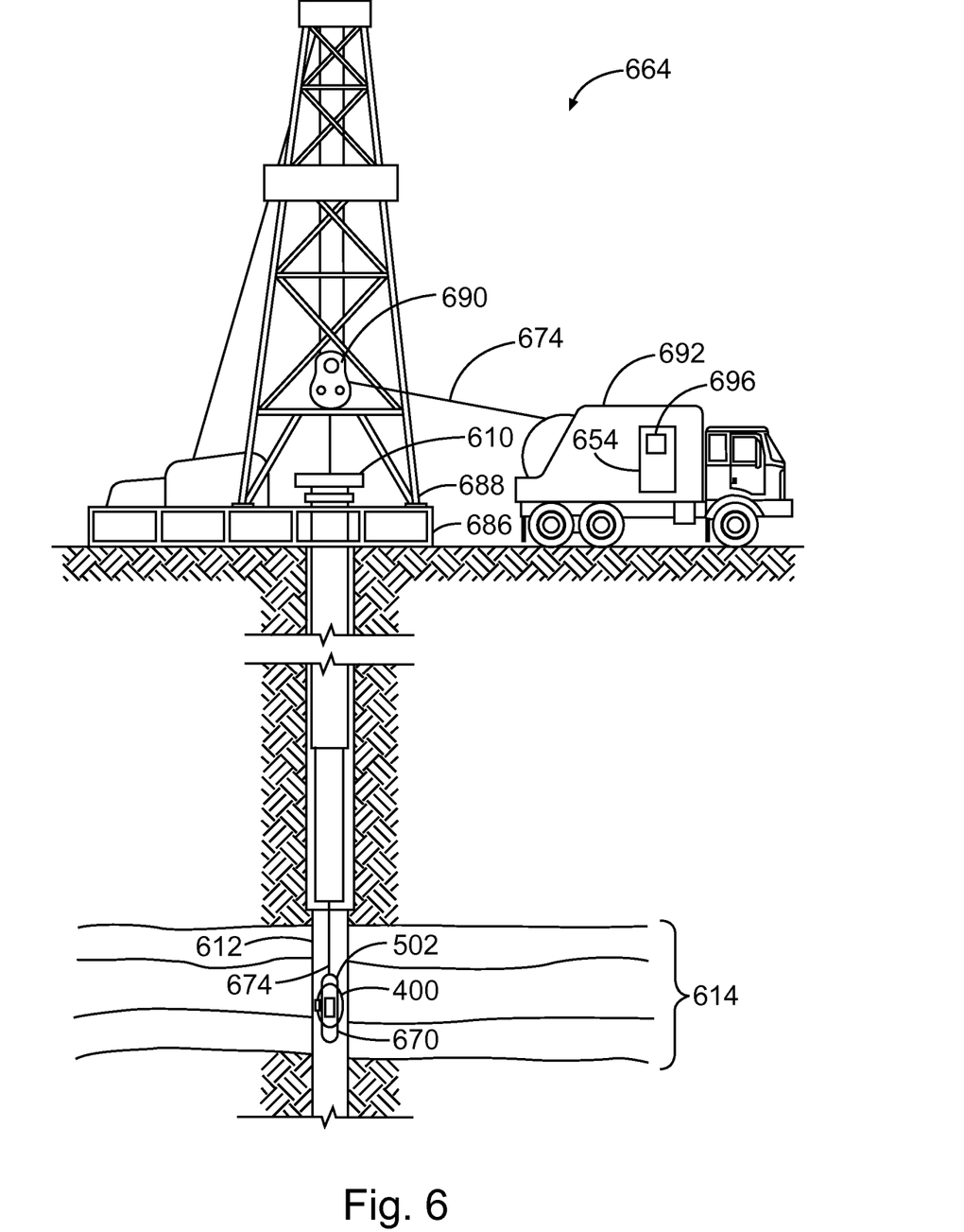
FIG. 6 illustrates a wireline system embodiment.
Figure 7:
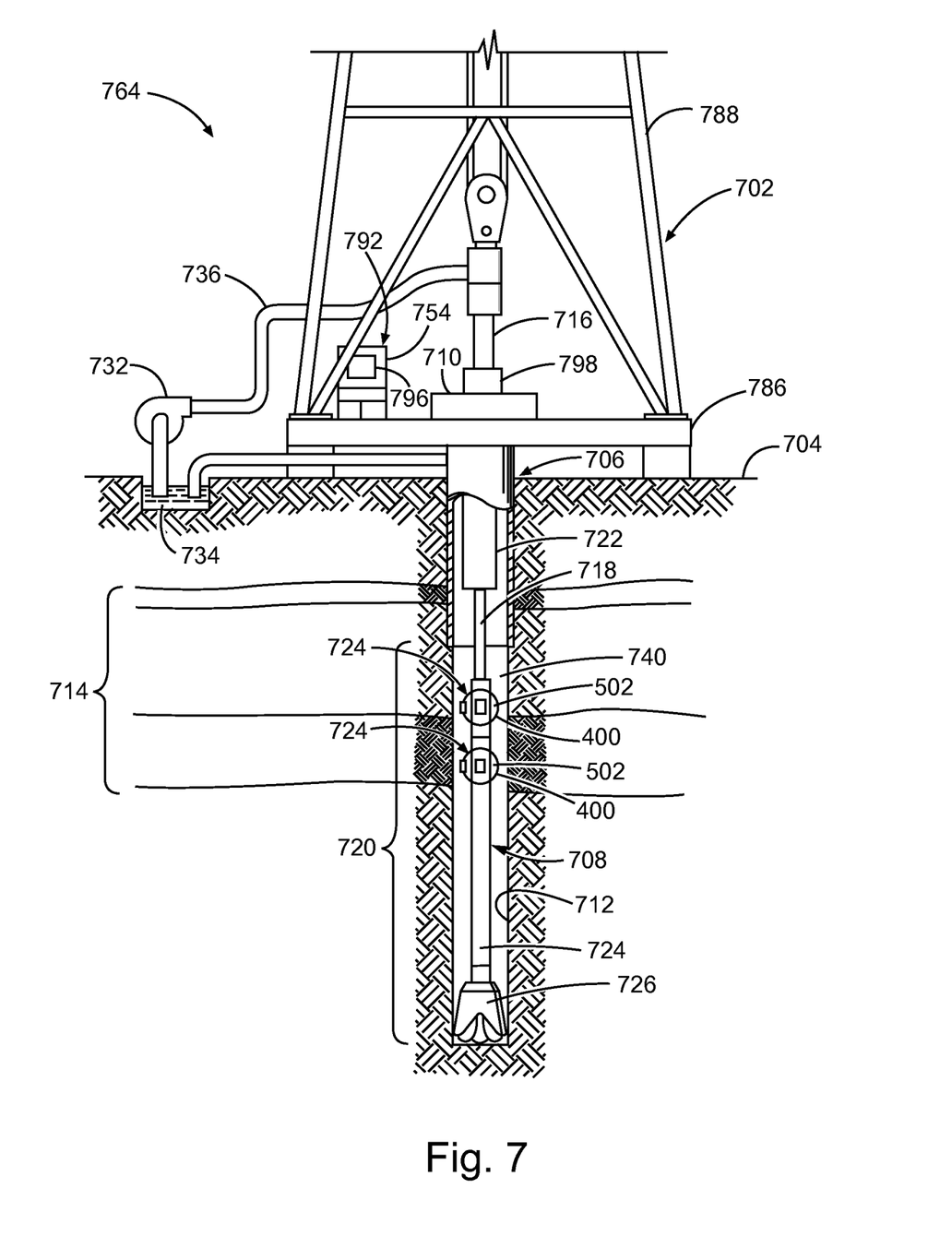
FIG. 7 illustrates a drilling rig system embodiment.

FIG. 6 illustrates a wireline system 664 and FIG. 7 illustrates a drilling rig system 764. Thus, the systems 664, 764 may comprise portions of a wireline logging tool body 670 as part of a wireline logging operation, or of a downhole tool 400 as part of a down hole drilling operation.

FIG. 6 shows a well during wireline logging operations. In this case, a drilling platform 686 is equipped with a derrick 688 that supports a hoist 690.

Drilling oil and gas wells is commonly carried out using a string of drill pipes connected together so as to form a drilling string that is lowered through a rotary table 610 into a wellbore or borehole 612. Here it is assumed that the drilling string has been temporarily removed from the borehole 612 to allow a wireline logging tool body 670, such as a probe or sonde, to be lowered by wireline or logging cable 674 into the borehole 612. Typically, the wireline logging tool body 670 is lowered to the bottom of the region of interest and subsequently pulled upward at a substantially constant speed.

During an upward or downward trip, at a series of depths, the instruments (e.g., the apparatus 400 of FIG. 4 and/or system 502 of FIG. 5) included in the tool body 670 may be used to perform borehole evaluations within the borehole 612 (e.g. making one or more measurements of the formation 614, cement (not shown), a casing (not shown), or other downhole features or components). The measurement data can be communicated to a surface logging facility 692 for storage, processing, and analysis. The logging facility 692 may be provided with electronic equipment for various types of signal processing, such as ultrasonic signal decomposition, which may be implemented by any one or more of the components of the apparatus 400 of FIG. 4 and/or system 502 in FIG. 5. Similar formation evaluation data may be gathered and analyzed during drilling operations (e.g., during LWD (logging while drilling) operations, MWD (measurement while drilling) operations, and by extension, sampling while drilling).

In some embodiments, the tool body 670 comprises the apparatus 400 for obtaining and analyzing acoustic noise measurements from a subterranean formation through a borehole. The tool body 670 is suspended in the wellbore by a wireline cable 674 that connects the tool body 670 to a surface control unit (e.g., comprising a workstation 654). The tool body 670 with the apparatus 400 may be deployed in the borehole 612 on coiled tubing, jointed drill pipe, hard wired drill pipe, or any other suitable deployment technique.

FIG. 7 illustrates how a system 764 may also form a portion of a drilling rig 702 located at the surface 704 of a well 706. The drilling rig 702 may provide support for a drill string 708. The drill string 708 may operate to penetrate the rotary table 710 for drilling the borehole 712 through the subsurface formations 714. The drill string 708 may include a Kelly 716, drill pipe 718, and a bottom hole assembly 720, perhaps located at the lower portion of the drill pipe 718.

The bottom hole assembly 720 may include drill collars 722, a down hole tool 724, and a drill bit 726. The drill bit 726 may operate to create the borehole 712 by penetrating the surface 704 and the subsurface formations 714. The downhole tool 724 may comprise any of a number of different types of tools including MWD tools, LWD tools, and others.

During drilling operations, the drill string 708 (perhaps including the Kelly 716, the drill pipe 718, and the bottom hole assembly 720) may be rotated by the rotary table 710. Although not shown, in addition to, or alternatively, the bottom hole assembly 720 may also be rotated by a motor (e.g., a mud motor) that is located down hole. The drill collars 722 may be used to add weight to the drill bit 726. The drill collars 722 may also operate to stiffen the bottom hole assembly 720, allowing the bottom hole assembly 720 to transfer the added weight to the drill bit 726, and in turn, to assist the drill bit 726 in penetrating the surface 704 and subsurface formations 714.

During drilling operations, a mud pump 732 may pump drilling fluid (sometimes known by those of ordinary skill in the art as "drilling mud") from a mud pit 734 through a hose 736 into the drill pipe 718 and down to the drill bit 726. The drilling fluid can flow out from the drill bit 726 and be returned to the surface 704 through an annular area 740 between the drill pipe 718 and the sides of the borehole 712. The drilling fluid may then be returned to the mud pit 734, where such fluid is filtered. In some embodiments, the drilling fluid can be used to cool the drill bit 726, as well as to provide lubrication for the drill bit 726 during drilling operations. Additionally, the drilling fluid may be used to remove subsurface formation cuttings created by operating the drill bit 726.

The downhole tool 724 can comprise the apparatus 400 as discussed previously with reference to FIG. 4. The downhole tool 400 can be used to perform borehole evaluations during the drilling process.

For example, in some embodiments, a system 502, 664, 764 may comprise a housing and one or more apparatus 400 attached to the housing with a rotatable mount associated with an axis of rotation (e.g., the axis L shown in FIG. 4). The apparatus 400 attached to the housing can be constructed and operated as described previously.

The housing can be used in wireline or MWD/LWD applications. Thus, the housing may comprise one of a wireline tool body, a measurement while drilling downhole tool, or a logging while drilling downhole tool.

Such modules may include hardware circuitry, and/or a processor and/or memory circuits, software program modules and objects, and/or firmware, and combinations thereof, as desired by the architect of the apparatus 400 and systems 502, 664, 764 and as appropriate for particular implementations of various embodiments. For example, in some embodiments, such modules may be included in an apparatus and/or system operation simulation package, such as a signal propagation simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 400 and systems 502, 664, 764 are intended to provide a general understanding of the structure of various embodiments, and they are not intended to serve as a complete description of all the elements and features of apparatus and systems that might make use of the structures described herein.

The systems 502, 664, 764 can include a non-transitory machine-readable storage device can comprise instructions stored thereon, which, when performed by a machine, cause the machine to perform operations, the operations comprising one or more features similar to or identical to features of methods and techniques related to ultrasonic signal decomposition for borehole evaluation or pipeline inspection. These operations include any one or all of the operations forming the methods shown in FIGS. 2 and 3. The physical structure of such instructions may be operated on by one or more processors.

A machine-readable storage device, herein, is a physical device that stores data represented by physical structure within the device. Examples of non-transitory machine-readable storage devices can include, but are not limited to, read only memory (ROM), random access memory (RAM), a magnetic disk storage device, an optical storage device, a flash memory, and other electronic, magnetic, and/or optical memory devices.

Traditional methods to determine the thickness of a casing is to use a peak frequency of a recorded wave reverberation. This approach is typically limited to thin casing and relative large diameter pipelines. For evaluating the cement-casing bond, the traditional cement bond log uses the normal-incident plane-wave theory to calculate the acoustic impedance behind the casing. This theory does not consider either the curvature of the casing wall or the transducer's beam spreading. In addition, the cement bond impedance is calculated based on a resonance response. This can limit the area of applicability of traditional methods to relatively thin casings.

The apparatus, systems, and methods disclosed herein may provide a new signal analysis approach for ultrasonic borehole evaluation and pipeline inspection based on signal decomposition. The adopted translation-invariant matching pursuit decomposition decomposes a measured ultrasonic waveform into distinct reflection and reverberation echoes and/or wave packages (e.g., wavelets). This can be accomplished robustly in the presence of measurement errors and noise. The decomposed wavelets can be directly used for a variety of purposes in borehole evaluation and pipeline inspection, including casing/pipeline ID, casing/pipeline thickness, cement bonding impedance, borehole image, pipeline corrosion, and pipeline welding condition.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method for borehole evaluation or pipeline inspection, the method comprising:
receiving an ultrasonic signal in response to a transmitted signal;
generating a set of non-orthogonal basis functions based on a synthetic signal generated from properties of a physical model of a pipeline and the transmitted signal;
decomposing the ultrasonic signal into at least one wavelet using a constrained matching pursuit decomposition and the set of non-orthogonal basis functions as constraint parameters;
determining parameters associated with each wavelet; and
performing the borehole evaluation or pipeline inspection based on the parameters.

2. The method of claim 1, wherein performing the borehole evaluation comprises performing borehole imaging, casing inspection, or determining casing inside diameter using the parameters.

3. The method of claim 1, wherein performing the pipeline inspection comprises performing pipeline flaw detection or pipeline inside diameter.

4. The method of claim 2, wherein the parameters comprise amplitude, phase, arrival time, scaling factor, and frequency of an associated wavelet.

5. The method of claim 4, further comprising performing the borehole imaging and casing inspection using the amplitude, the phase, and the arrival time of the associated wavelet.

6. The method of claim 1, wherein the set of basis functions comprises Gabor basis functions.

7. The method of claim 1, wherein decomposing the ultrasonic signal comprises determining the set of basis functions that are equal to the wavelets in waveform shape.

8. The method of claim 1, further comprising performing borehole imaging, casing inspection, casing inside diameter, pipeline flaw detection, or pipeline inside diameter using the parameters of the associated wavelet based on a first echo of the at least one echo or guided wave packages.

9. The method of claim 8, further comprising determining cement impedance, casing thickness, or pipeline thickness in response to the parameters of the associated wavelets based on reverberation echoes subsequent to the first echo or distinct wave packages of guided waves.

10. The method of claim 1, further comprising performing pipeline welding inspections or corrosion detection in response to parameters associated with wavelets based on wave packages of guided waves.

11. The method of claim 1, further comprising:
performing waveform compression based on the parameters; and
storing the compressed waveforms.

12. An apparatus for performing a borehole evaluation or pipeline inspection, the apparatus comprising:
an acoustic transducer;
an acoustic receiver; and
a processor communicably coupled to a memory device, the memory device containing a set of instructions that, when executed by the processor, cause the processor to:
receive a reflected signal from the acoustic receiver, the reflected signal corresponding to an acoustic signal transmitted by the acoustic transducer;
generate a set of non-orthogonal basis functions based on a synthetic signal generated from properties of a physical model of a pipeline and the transmitted acoustic signal;
decompose the acoustic signal into at least one wavelet using a constrained matching pursuit decomposition and the set of non-orthogonal basis functions as constraint parameters;
determine parameters associated with each wavelet; and
perform the borehole evaluation or pipeline inspection based on the parameters.

13. The apparatus of claim 12, wherein the acoustic transducer and receiver are part of a pulse-echo device.

14. The apparatus of claim 12, wherein the acoustic transducer and receiver includes a plurality of receivers that are all part of a pitch-catch device.

15. The apparatus of claim 12, wherein the processor is further to perform the borehole evaluation or pipeline inspection based on a subset of the parameters in response to which of the borehole evaluation or the pipeline inspection is being performed.

16. A system, comprising:
a housing;
an apparatus attached to the housing with a rotatable mount associated with an axis of rotation, the apparatus comprising an acoustic transducer attached to the rotatable mount transmits an ultrasonic signal and receives a plurality of echoes or wave packages; and
a processor communicably coupled to the apparatus, processor coupled to memory containing a set of instruction that, when executed by the processor, cause the processor to
receive a reflected signal from the acoustic transducer, the reflected signal corresponding to an acoustic signal transmitted by the acoustic transducer;
generate a set of non-orthogonal basis functions based on a synthetic signal generated from properties of a physical model of a pipeline and the transmitted acoustic signal;
decompose the reflected signal into wavelets using a constrained matching pursuit decomposition and the set of non-orthogonal basis functions as constraint parameters;
determine parameters associated with each wavelet; and
evaluate a borehole or a pipeline based on the parameters.

17. The system of claim 16, wherein the housing comprises:
one of a wireline tool body, a measurement while drilling down hole tool, or a logging while drilling down hole tool.

18. The system of claim 16, wherein the rotatable mount is also attached to a drill string.

19. The system of claim 16, wherein the set of instructions further cause the processor is to: generate a synthetic signal based on the physical model of the pipeline, decompose the synthetic signal, use the matching pursuit method and the set of basis functions that are substantially similar to the plurality of echoes in waveform shape, in order to generate the constraint parameters, perform the decomposition, using the constraint parameters, of the received plurality of echoes as the parameter constrained decomposition of the received plurality of echoes into the plurality of wavelets.

20. The system of claim 19, wherein the set of instructions further cause the processor is to: perform the decomposition, using the constraint parameters, to determine an energy and estimated energy decay of the received plurality of echoes to estimate the impedance of the cement-casing bond.

* * * * *